(12) United States Patent
Miyashita et al.

(10) Patent No.: US 8,246,800 B2
(45) Date of Patent: Aug. 21, 2012

(54) GAS SENSOR

(75) Inventors: Takeya Miyashita, Aichi (JP); Takashi Ito, Aichi (JP)

(73) Assignee: NGK Insulators, Ltd., Nagoya (JP)

( * ) Notice: Subject to any disclaimer, the term of this patent is extended or adjusted under 35 U.S.C. 154(b) by 251 days.

(21) Appl. No.: 12/410,727

(22) Filed: Mar. 25, 2009

(65) Prior Publication Data

US 2009/0242404 A1    Oct. 1, 2009

(30) Foreign Application Priority Data

Mar. 28, 2008  (JP) .................................. 2008-085940
Mar. 28, 2008  (JP) .................................. 2008-085941

(51) Int. Cl.
   *G01N 27/26*  (2006.01)
(52) U.S. Cl. ......... 204/429; 204/424; 204/427; 204/428
(58) Field of Classification Search .......... 204/421–420, 204/410, 411, 421–429; 205/781, 783.5–785, 205/787
   See application file for complete search history.

(56) References Cited

U.S. PATENT DOCUMENTS

| | | | |
|---|---|---|---|
| 6,205,843 B1 | 3/2001 | Tanaka et al. | |
| 6,355,152 B1 * | 3/2002 | Kato et al. | 204/425 |
| 2002/0060151 A1 | 5/2002 | Kato et al. | |
| 2003/0136674 A1 | 7/2003 | Kato et al. | |
| 2003/0188968 A1 | 10/2003 | Naito et al. | |
| 2004/0069629 A1 | 4/2004 | Tanaka et al. | |
| 2004/0231985 A1 | 11/2004 | Kato et al. | |
| 2007/0108049 A1 * | 5/2007 | Wahl et al. | 204/424 |
| 2007/0235332 A1 * | 10/2007 | Sugiyama et al. | 204/424 |
| 2008/0237064 A1 | 10/2008 | Nakasone et al. | |
| 2009/0120791 A1 | 5/2009 | Miyashita et al. | |
| 2009/0242404 A1 | 10/2009 | Miyashita et al. | |

FOREIGN PATENT DOCUMENTS

| | | |
|---|---|---|
| EP | 1 260 814 A2 | 11/2002 |
| EP | 1 310 788 A1 | 5/2003 |
| EP | 1 464 954 A2 | 10/2004 |
| JP | 64-078148 A1 | 3/1989 |
| JP | 2000-028576 A1 | 1/2000 |
| JP | 2000-180410 A1 | 6/2000 |
| JP | 2000-275215 A1 | 10/2000 |
| JP | 2001-281210 A1 | 10/2001 |
| JP | 2004-003964 A1 | 1/2004 |
| JP | 2004-132960 A1 | 4/2004 |
| JP | 2004-354400 A1 | 12/2004 |
| JP | 2006-284223 A1 | 10/2006 |
| JP | 2008-008668 A1 | 1/2008 |

(Continued)

*Primary Examiner* — Jeffrey T Barton
*Assistant Examiner* — Maris R Kessel
(74) *Attorney, Agent, or Firm* — Burr & Brown

(57) ABSTRACT

A gas sensor for detecting a predetermined gas component in a measurement gas includes a sensor element in which an opening of a first gas inlet and an opening of a second gas inlet for introducing the measurement gas from an outside are provided at one end. The openings are elongated and substantially rectangular. A sum of sizes in a lateral direction of the openings is greater than or equal to 8 μm and less than or equal to 60 μm, and a sum of areas of the openings is greater than or equal to 0.02 mm$^2$ and less than or equal to 0.1 mm$^2$. The sizes in the lateral direction and the areas of the openings are set to be within a preferable range so that the water droplets attached on the forward end surface can be prevented from entering into the sensor element through the openings.

14 Claims, 8 Drawing Sheets

FOREIGN PATENT DOCUMENTS

| | | |
|---|---|---|
| JP | 2009-236833 A1 | 10/2009 |
| JP | 2009-236835 A1 | 10/2009 |
| WO | 2007/119311 A1 | 10/2007 |
| WO | 2008/007706 A1 | 1/2008 |

* cited by examiner

F I G . 6
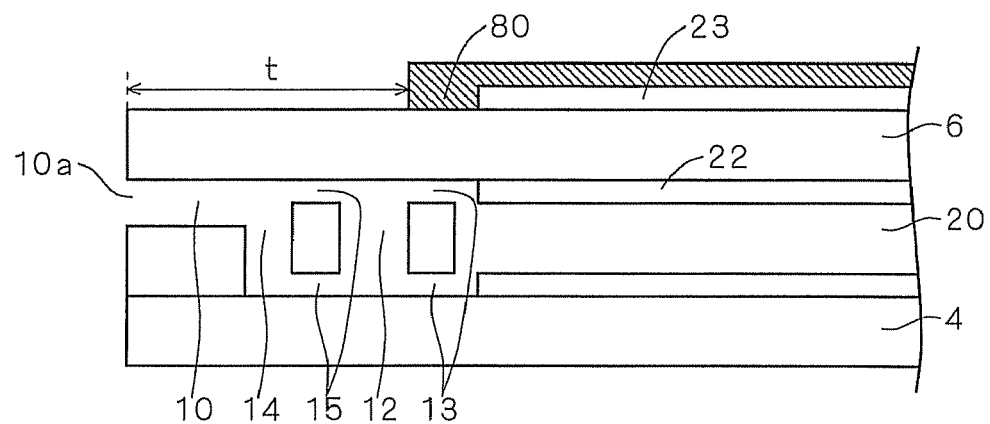
F I G . 7
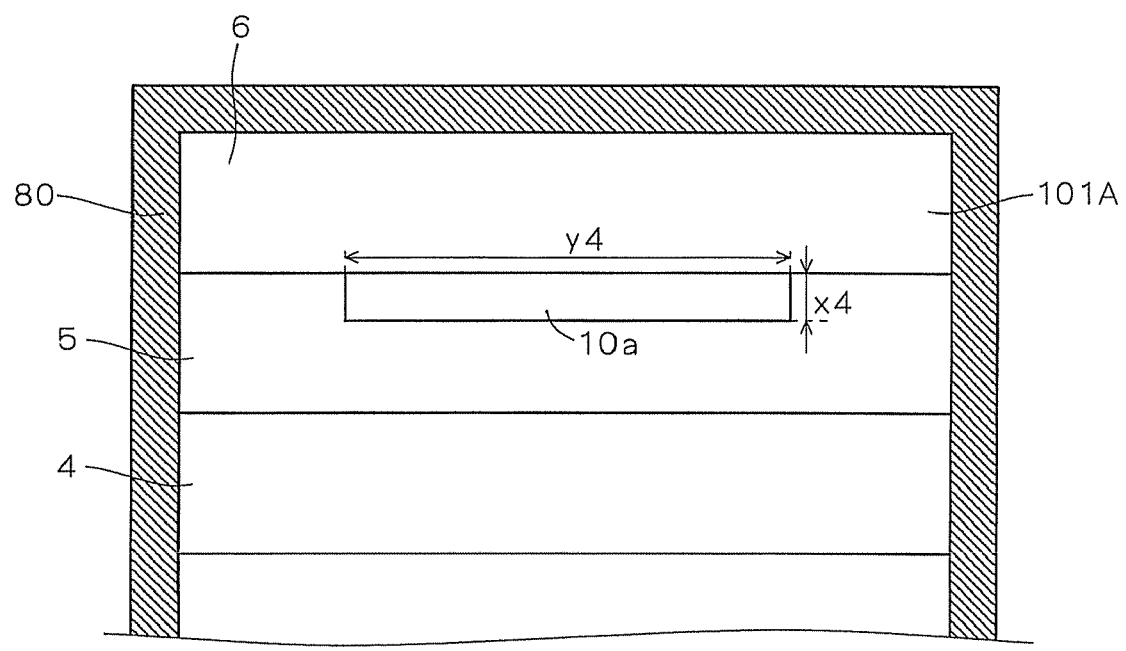

GAS SENSOR

BACKGROUND OF THE INVENTION

1. Field of the Invention

The present invention relates to a gas sensor for measuring a concentration of a predetermined gas component in a measurement gas, specifically to a gas sensor for measuring a concentration of nitrogen oxide (NOx).

2. Description of the Background Art

Conventionally, various measuring devices have been used for finding out a concentration of a desired gas component in a measurement gas. A known device of measuring a NOx concentration in a measurement gas such as a combustion gas, for example, is a gas sensor having a Pt-containing electrode and a Rh-containing electrode formed on an oxygen ion conductive solid electrolyte, such as zirconia ($ZrO_2$) (see Japanese Patent Application Laid-Open No. 2006-284223, for example).

SUMMARY OF THE INVENTION

The present invention is directed to a gas sensor for detecting a predetermined gas component in a measurement gas.

According to the present invention, a gas sensor includes: a sensor element; and one or more openings provided at one end of the sensor element, for introducing the measurement gas from an outside, wherein the one or more openings are elongated and substantially rectangular, and a sum of sizes in a lateral direction of the one or more openings is greater than or equal to 8 μm and less than or equal to 60 μm.

The size in the lateral direction of the opening is set to be in a preferable range so that the water droplets attached on a forward end surface can be prevented from entering into an inside of the sensor element through the opening.

Preferably, the gas sensor includes a porous layer provided in a side surface of the sensor element so as to cover a region of the other end of the sensor element from a position which is apart from the one end of the sensor element greater than or equal to 2 mm toward the other end portion of the sensor element, the porous layer being consisted of a porous body having a higher porosity than a constituent material for a surface of the sensor element, wherein the surface of the sensor element is consisted of a dense material having water-repellency as a main component.

When using the one end of the gas sensor toward vertically above, even if the water droplets are attached on a region of the side surface of the sensor element where the porous layer is not formed, these water droplets are moved and absorbed into the porous layer to be dispersed inside the porous layer. Thereby, the water droplets are prevented from moving to the element end surface and from entering into the sensor element.

According to the present invention, the gas sensor includes a sensor element and one or more openings provided at one end of the sensor element, for introducing the measurement gas from an outside, wherein a sum of an area of the one or more openings is greater than or equal to 0.02 $mm^2$ and less than or equal to 0.1 $mm^2$.

The area of the opening is set to be in a preferable range so that the water droplets attached on the forward end surface can be prevented from entering into an inside of the sensor element through the opening.

It is therefore an object of the present invention to prevent condensate water from entering into the sensor element and to provide a gas sensor in which the deterioration of the measurement accuracy due to a temporal use is suppressed.

BRIEF DESCRIPTION OF THE DRAWINGS

FIG. 6 is a partly enlarged view for schematically showing a configuration of a gas sensor according to a fourth preferred embodiment.

FIG. 7 is a view for showing a sensor element according to the fourth preferred embodiment seen from a side of the element end surface.

DETAILED DESCRIPTION OF THE INVENTION

First Preferred Embodiment

Outline Configuration of Gas Sensor

Figure 1:
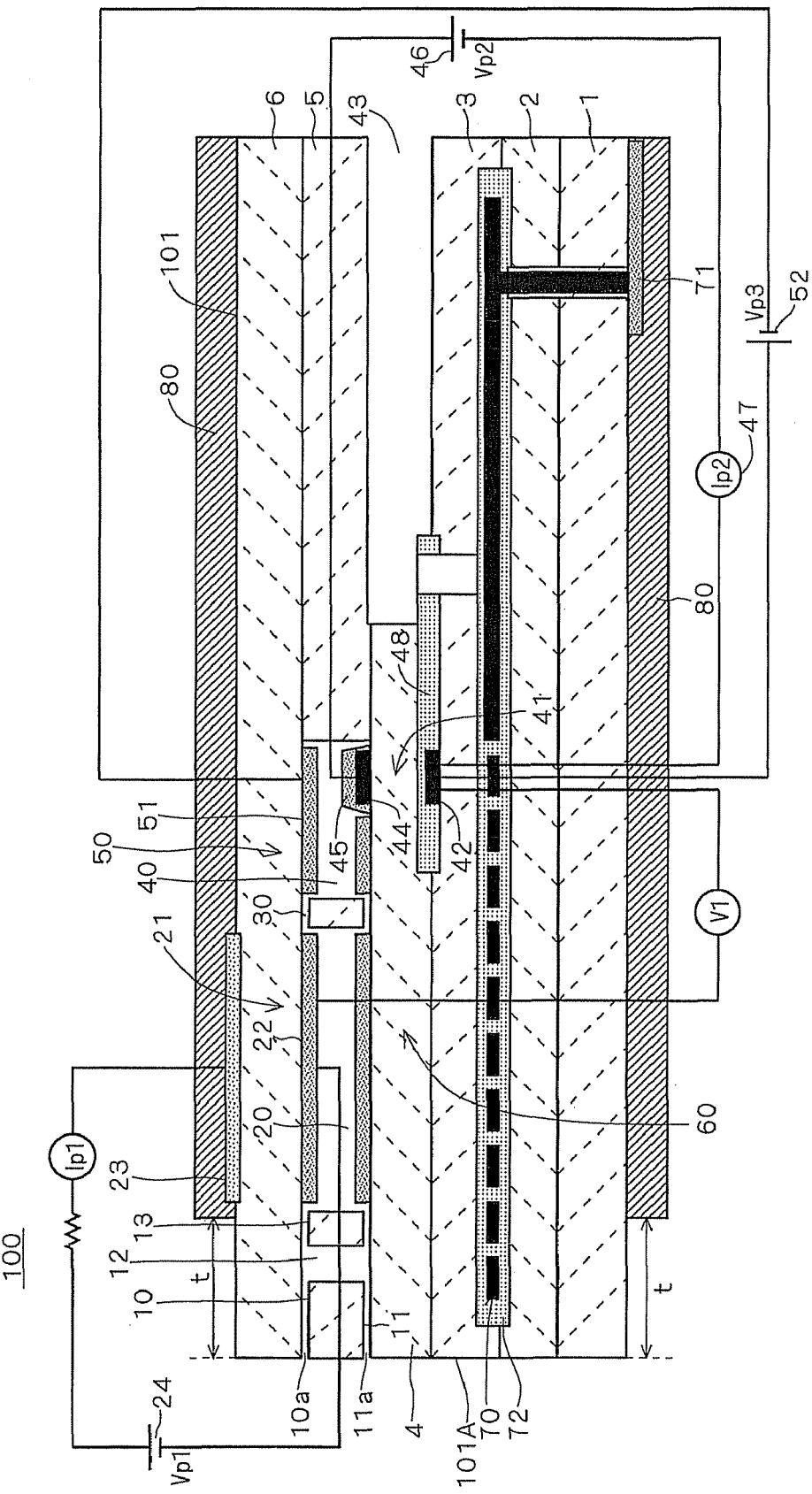
FIG. 1 is a sectional view for schematically showing a configuration of a gas sensor.

FIG. 1 is an outline sectional schematic view for showing a configuration of a gas sensor 100 which is one example of the gas sensor according to the present invention. The gas sensor 100 detects a predetermined gas component in a gas which is an object of measurement (a measurement gas), and further, measures a concentration thereof. The present embodiment will be described taking an example where the gas sensor 100 is a NOx sensor detecting nitrogen oxide (NOx) as an object component. The gas sensor 100 includes a sensor element 101 consisted of an oxygen ion conductive solid electrolyte such as zirconia ($ZrO_2$). A solid electrolyte such as zirconia composing the sensor element 101 is formed to be dense, and has water-repellency so that the water droplets attached on a surface of the solid electrolyte is not to be absorbed into the element.

The sensor element 101 shown in FIG. 1 includes a structure in which a first substrate layer 1, a second substrate layer 2, a third substrate layer 3, a first solid electrolyte layer 4, a spacer layer 5, and a second solid electrolyte layer 6 are laminated in this order from a bottom seen in FIG. 1, each of the layers being consisted of an oxygen ion conductive solid electrolyte. The sensor element 101 is manufactured, for example, by laminating ceramics green sheets which correspond to each layer, cutting them into a predetermined size and burning them after performing a predetermined process and pattern printing on them.

A first gas inlet 10, a second gas inlet 11 (hereinafter, the first gas inlet 10 and the second gas inlet 11 are collectively referred to as a gas inlet part), a first buffer space 12, a first diffusion control part 13, a first internal space 20, a second diffusion control part 30 and a second internal space 40 are adjacently formed in this order in communication with one another between a lower surface of the second solid electrolyte layer 6 and an upper surface of the first solid electrolyte layer 4 at one end of the sensor element 101. Hereinafter, an edge part of the sensor element 101 at a side where the first gas inlet 10 and the second gas inlet 11 are provided is referred to as an element end.

The first buffer space 12, the first internal space 20 and the second internal space 40 are provided by hollowing out the spacer layer 5, which is precisely an internal space with an upper portion sectioned by the lower surface of the second solid electrolyte layer 6, an lower portion sectioned by the upper surface of the first solid electrolyte layer 4, and a side portion sectioned by a side surface of the spacer layer 5. Each of the first gas inlet 10, the second gas inlet 11, the first diffusion control part 13, and the second diffusion control part 30 is provided as two horizontally long slits (with an opening having a longitudinal direction in a direction perpendicular to FIG. 1) arranged one above the other. A part from the first gas inlet 10 and the second gas inlet 11 to the second internal space 40 is also referred to as a gas distribution part.

The first gas inlet 10 and the second gas inlet 11 bring in the measurement gas from the outside into the inside of the sensor element 101, thereby to introduce the measurement gas to the first buffer space 12 with a predetermined diffusion resistance. The first gas inlet 10 includes an opening 10a which is open to the outside on a surface of an end of the sensor element 101 (a forward end surface 101A). The second gas inlet 11 includes an opening 11a which is open to the outside on the forward end surface 101A.

Since the openings 10a and 11a are formed into a horizontally-long slit shape having a predetermined size, i.e. elongated and substantially rectangular in the gas sensor 100, condensate water attached on the forward end surface 101A is prevented from entering into the sensor element 101. Details on preventing condensate water from entering into the element will be described later.

The first buffer space 12 is provided in order to counteract concentration fluctuation of the measurement gas caused by pressure fluctuation of the measurement gas in the outside (pulsation of exhaust pressure if a measurement gas is an emission gas of automobiles).

The first diffusion control part 13 provides a predetermined diffusion resistance to the measurement gas brought into the first diffusion control part 13 from the first buffer space 12.

The first internal space 20 is provided as a space for controlling oxygen partial pressure in the measurement gas introduced through the first diffusion control part 13. The oxygen partial pressure is controlled by operating a main pump cell 21.

The main pump cell 21 is an electrochemical pump cell composed of an inside pump electrode 22 provided on an almost whole surface in a part of the lower surface of the second solid electrolyte layer 6 facing the first internal space 20, an outside pump electrode 23 provided in a region corresponding to the inside pump electrode 22 on an upper surface of the second solid electrolyte layer 6 to be exposed to the outside, and a part of the second solid electrolyte layer 6 interposed between those electrodes. The inside pump electrode 22 and the outside pump electrode 23 are formed as porous cermet electrodes (e.g. cermet electrodes of Pt and $ZrO_2$ including Au by 1%) which are oblong in a plane view. Further, the inside pump electrode 22 is formed using material in which reduction ability to an NO component in the measurement gas is weakened, or material without reduction ability.

The main pump cell 21 is provided with a variable power source 24 outside the sensor element 101. The variable power source 24 applies a desired pump voltage $Vp1$ between the inside pump electrode 22 and the outside pump electrode 23 to flow a pump current $Ip1$ in a positive direction or a negative direction between the outside pump electrode 23 and the inside pump electrode 22, allowing to pump out oxygen in the first internal space 20 to the outside or to pump in oxygen in the outside into the first internal space 20.

The second diffusion control part 30 provides a predetermined diffusion resistance to the measurement gas brought into the second internal space 40 from the first internal space 20.

The second internal space 40 is provided as a space for performing a process to measure concentration of nitrogen oxide (NOx) in the measurement gas introduced through the second diffusion control part 30.

A NOx concentration can be measured by operating a measuring pump cell 41. The measuring pump cell 41 is an electrochemical pump cell composed of a reference electrode 42 between the upper surface of the third substrate layer 3 and the first solid electrolyte layer 4, a measuring electrode 44 provided on the upper surface of the first solid electrolyte layer 4 facing the second internal space 40, spaced apart from the second diffusion control part 30, and the first solid electrolyte layer 4. Each of the reference electrode 42 and the measuring electrode 44 is a porous cermet electrode which is substantially oblong in a plane view. The reference electrode 42 is surrounded by an air induction layer 48 consisted of porous alumina and leading to a reference gas introduction space. The measuring electrode 44 is composed of porous cermet of metal resolving NOx which is a measurement gas component, and zirconia. Thus, the measuring electrode 44 serves as a NOx reduction catalyst for resolving NOx in the atmosphere of the second internal space 40.

Moreover, the measuring electrode 44 is covered with a third diffusion control part 45. The third diffusion control part 45 is a porous and alumina-containing film, and functions to limit the amount of NOx flowing into the measuring electrode 44.

The measuring pump cell 41 is provided with a DC power source 46 applying a pump voltage $Vp2$ which is a fixed voltage between the measuring electrode 44 and the reference electrode 42 to resolve NOx. Thereby, oxygen is generated in the atmosphere of the second internal space 40, and then, the oxygen is pumped out to the reference gas inlet space 43. A pump current $Ip2$ allowed to flow by the operation of the measuring pump cell 41 is detected by an ammeter 47.

Oxygen partial pressure is previously controlled in the first internal space 20, and thereafter, oxygen partial pressure in the measurement gas introduced through the second diffusion control part 30 is further controlled in the second internal space 40 by an auxiliary pumping cell 50. Accordingly, the gas sensor 100 can perform the measurement of a NOx concentration with high accuracy.

The auxiliary pump cell 50 is an auxiliary electrochemical pump cell composed of an auxiliary pump electrode 51 provided on substantially whole surface in a part of the lower surface of the second solid electrolyte layer 6 facing the second internal space 40, the second solid electrolyte layer 6, the spacer layer 5, the first solid electrolyte layer 4 and the reference electrode 42.

Similarly to the inside pump electrode 22, the auxiliary pump electrode 51 is formed using material in which reduction ability to an NO component in the measurement gas is weakened, or material without reduction ability.

The auxiliary pump cell 50 is provided with a DC power source 52 outside the sensor element 101. The DC power source 52 applies a fixed voltage Vp3 between the auxiliary pump electrode 51 and the reference electrode 42 to pump out oxygen in the atmosphere of the second internal space 40 into the reference gas inlet space 43.

The sensor element 101 further includes an oxygen partial pressure detecting sensor cell 60 which is an electrochemical pump cell composed of the inside pump electrode 22, the reference electrode 42, the second solid electrolyte layer 6, the spacer layer 5 and the first solid electrolyte layer 4.

The oxygen partial pressure detecting sensor cell 60 detects oxygen partial pressure in the atmosphere of the first internal space 20 based on an electromotive force V1 generated between the inside pump electrode 22 and the reference electrode 42 which is caused by the difference of oxygen concentration between the atmosphere of the first internal space 20 and a reference gas (air) of the reference gas inlet space 43. The detected oxygen partial pressure is used for feedback controlling the variable power source 24. Specifically, a pump voltage applied to the main pump cell 21 is controlled so as to set oxygen partial pressure in the atmosphere of the first internal space 20 at a predetermined value which is lower enough to control oxygen partial pressure in the second internal space 40.

The sensor element 101 further includes a heater 70 formed to be interposed between the second substrate layer 2 and the third substrate layer 3 from above and below. The heater 70 generates heat by power feeding from outside through a heater electrode 71 provided on a lower surface of the first substrate layer 1. Heat generation by the heater 70 allows to enhance oxygen ion conductivity of solid electrolyte composing the sensor element 101. The heater 70 is buried over the whole area from the first internal space 20 to the second internal space 40 so that a predetermined area of the sensor element 101 is heated and kept warm at a predetermined temperature. A heater insulating layer 72 consisted of alumina or the like is formed on an upper surface and a lower surface of the heater 70 in order to obtain electronic insulation between the second substrate layer 2 and the third substrate layer 3.

In the gas sensor 100 having the above described configuration, the measurement gas is provided with the measuring pump cell 41, with oxygen partial pressure constantly maintained at a fixed low value (a value substantially not affecting the measurement of NOx) by operating the main pump cell 21 and the auxiliary pump cell 50. Accordingly, a pump current flowing in the measuring pump cell 41 by pumping out oxygen generated by a reduction of NOx is to be substantially proportional to the reduced NOx concentration, thereby allowing to find out NOx concentration in the measurement gas.

In the gas sensor 100, a porous layer 80 consisted of a porous body is formed on four side surfaces (i.e. side surfaces sharing an edge with the forward end surface 101A) in the longitudinal direction of the sensor element 101 (a right and left direction seen in FIG. 1) for purposes of such as protection of the outside pump electrode 23. In FIG. 1, only porous layers formed on the upper surface and lower surface of the sensor element 101 are shown.

The porous layer 80 is formed of a porous body having a higher porosity at least than a solid electrolyte composing the sensor element 101, and preferably formed of a porous body consisted of at least one of alumina ($Al_2O_3$), magnesium alumina spinel ($MgAl_2O_4$), and zirconia ($ZrO_2$) as a main component.

The porous layer 80 is formed so as to cover the side surface of the sensor element 101 including the outside pump electrode 23 in a region from a position apart from the forward end in a predetermined distance t in the longitudinal direction to an end of a side of the reference gas inlet space 43 (hereinafter, referred to as a backward end). In the gas sensor 100, because the porous layer 80 is formed as described above, the outside pump electrode 23 is protected by covering, and condensate water attached on the side surface of the sensor element 101 is prevented from moving and attaching on the forward end surface 101A. Details of suppressing condensate water reaching to the forward end surface 101A will be described later.

<Configuration of Gas Inlet>

Next, it will be described how to prevent the water droplets from entering into the sensor element 101 through the first gas inlet 10 and the second gas inlet 11. As described above, the first gas inlet 10 and the second gas inlet 11 include the openings 10a and 11a, respectively, on the forward end surface 101A.

Figure 2:
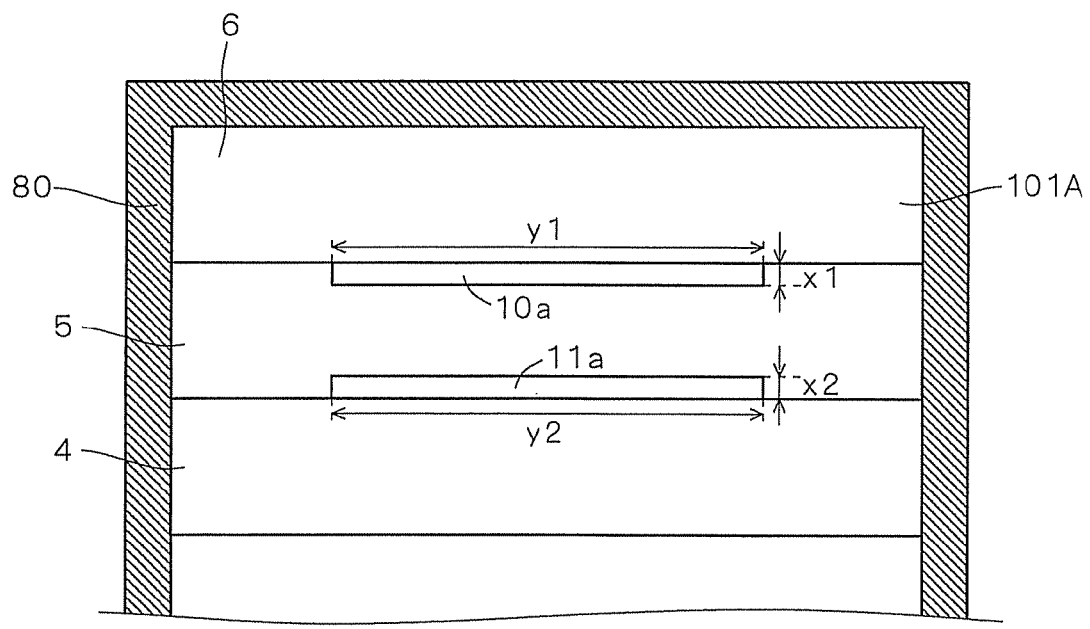
FIG. 2 is a view for showing a sensor element seen from an element end surface.

FIG. 2 is a view for showing the sensor element 101 seen from a side of the forward end surface 101A, illustrating how the first gas inlet 10 and the second gas inlet are formed. As shown in FIG. 2, the first gas inlet 10 includes the opening 10a which is a horizontally-long slit (elongated and substantially rectangular) provided to make contact with the lower surface of the second solid electrolyte layer 6. The second gas inlet 11 includes the opening 11a which is a horizontally-long slit (elongated and substantially rectangular) provided to male contact with the upper surface of the first solid electrolyte layer 4.

According to the present embodiment, the openings 10a and 11a for bringing external air into the sensor element 101 are provided on the forward end surface 101A as horizontally-long slits like the above with a preferable size, and therefore, water droplets attached on the forward end surface 101A is prevented from entering into the sensor element 101. By preventing the water droplets attached on the forward end surface 101A from entering into the sensor element 101, contaminants such as Mg and soot in the water droplets generated by condensing moisture in the emission gas can be prevented from entering into the sensor element 101, and further a clogging of the third diffusion control part 45 or the like covering the measuring electrode 44 for protection can be suppressed. Accordingly, deterioration of sensor output (pump current Ip2) due to such a clogging and deterioration of the measurement accuracy of the sensor caused thereby can be suppressed.

Practically, the preferable sizes of the openings 10a and 11a are each determined to be within a range that is both able to prevent the water droplets from entering into the sensor element 101 and to ensure the measurement responsiveness of the gas sensor 100 (the degree to perform measurement accurately and immediately following concentration change of the gas component to be an object of measurement).

In FIG. 2, x1 indicates a size in a vertical direction of the opening 10a, y1 indicates a size in a horizontal direction of the opening 10a, and x2 indicates a size in a vertical direction of the opening 11a, and y2 indicates a size in a horizontal direction of the opening 11a. Additionally, S1 represents an area of the opening 10a, and S2 represents an area of the opening 11a. In the present embodiment, the shape of the openings 10a and 11a is substantially rectangular so that the equations of S1=x1×y1 and S2=x2×y2 are established.

The range of sizes of the openings 10a and 11a where condensate water attached on the forward end surface 101A is preferably prevented from entering into the sensor element 101 and enough responsiveness of the sensor is ensured is shown below.

With respect to the openings 10a and 11a, when letting the sum of the sizes x1 and x2 of the vertical direction be X, it is preferable to set the value of X obtained by adding x1 and x2 greater than or equal to 8 μm and less than or equal to 60 μm. This is greater than or equal to one over one hundred fiftieth and less than or equal to one twentieth to a thickness of the sensor element 101. It is further preferable to set the summation X in a range of greater than or equal to 20 μm and less than or equal to 40 μm. This is greater than or equal to one sixtieth and less than or equal to one thirtieth to the thickness of the sensor element 101.

When letting the sum of areas of the openings 10a and 11a be S, it is preferable to set the value of S obtained by adding S1 and S2 greater than or equal to 0.02 mm² and less than or equal to 0.1 mm². This is greater than or equal to one over two hundred fifty fifth and less than or equal to one fifty first to the area of the element end surface 101A. It is further preferable to set the summation S in a range of greater than or equal to 0.05 mm² and less than or equal to 0.08 mm². This is greater than or equal to one over one hundred and second and less than or equal to one sixty fourth to the area of the forward end surface 101A.

In actual use of the gas sensor 100, the size of the water droplets attached on the forward end surface 101A is approximately more than 500 μm. Thus, the water droplets can be preferably prevented from entering in the range of the thickness and the area as described above.

<Configuration of Porous Layer>

Next, the porous layer 80 for preventing condensate water from attaching on the forward end surface 101A will be described. As described above, the porous layer 80 is formed on four side surfaces (i.e. side surfaces sharing an edge with the element end surface 101A) in the longitudinal direction of the sensor element 101 (a right and left direction seen in FIG. 1) with a predetermined thickness. The porous layer 80 is, for example, formed by applying a paste on a porous body on the element surface before burning in the process of manufacturing the sensor element 101, and thereafter performing burning.

When actually using the gas sensor 100 with being mounted on an emission system of an internal combustion in an automobile engine or the like, it is normally to be used with the end of the sensor element 101 shifting slightly toward vertically above. Accordingly, in the gas sensor 100 comprising the porous layer 80, the water droplets attached in a region of the distance t in the longitudinal direction from the forward end surface 101A on the element side surface are to move to the backward end of the sensor element 101, traveling along a solid electrolyte surface which is densely composed. Then the water droplets making contact with the porous layer 80 are absorbed into the porous layer 80 by capillarity of the porous body, and dispersed inside the porous layer 80. In actual use of the gas sensor 100, it is used at a temperature of about 800° C. so that the water droplets dispersed inside the porous layer 80 are sequentially evaporated.

As described above, the water droplets attached on the element side surface in the range of the distance t from the forward end surface 101A are to be absorbed into the porous layer 80, traveling along a solid electrolyte layer on a surface of the sensor element 101. This is why the water droplets are prevented from moving to and attaching on the forward end surface.

The above distance t is determined to be in a range to be able to suppress deterioration of sensor sensitivity caused by contaminants such as Mg clogging in the third diffusion control part 45. On the other hand, it is necessary to form the porous layer 80 to cover the outside pump electrode 23. Therefore, the preferable range of the distance t is greater than or equal to 2.0 mm in forming the porous layer 80. This is greater than or equal to one thirty fourth to the length of the longitudinal direction of the sensor element 101.

With the openings 10a and 11a having the configuration described above, in the gas sensor 100, the water droplets are prevented from entering into the sensor element 101 through the forward end, and in addition, the water droplets are prevented from moving to the forward end by the porous layer 80. This is why the water droplets are effectively prevented from entering into the sensor element 101. Therefore, contaminants such as Mg, soot and the like included in condensate water can be prevented from entering into the element, and further a clogging of the third diffusion control part 45 or the like covering the measuring electrode 44 for protection can be suppressed. Accordingly, deterioration of sensor output (pump current Ip2) due to such a clogging and deterioration of the measurement accuracy of the sensor caused thereby can be suppressed.

Second Preferred Embodiment

In the gas sensor 100 according to the first preferred embodiment, the first gas inlet 10 and the second gas inlet 11 include the openings 10a and 11a which are provided on the forward end surface 101A as two horizontally slits. Further, air brought in from the first gas inlet 10 and the second gas inlet 11 is introduced into the first internal space 20 through the first buffer space 12 and the first diffusion control part 13. In the second preferred embodiment, a second buffer space 14 and a fourth diffusion control part 15 are further provided between the gas inlet part and the first diffusion control part 13.

Figure 3:
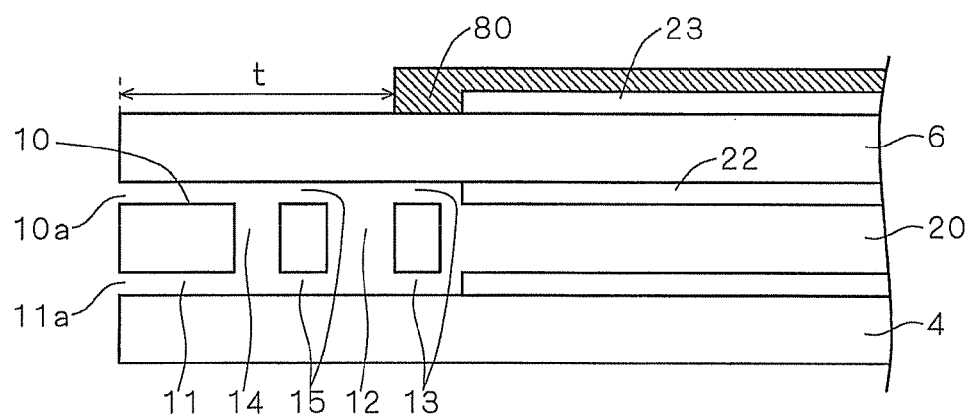
FIG. 3 is a partly enlarged view for schematically showing a configuration of a gas sensor according to a second preferred embodiment.

FIG. 3 is a partly enlarged view for schematically showing a configuration of the sensor element 101 according to the second preferred embodiment. Specifically, the first solid electrolyte layer 4, the spacer layer 5, the second solid electrolyte layer 6 and the porous layer 80 are seen from a bottom in FIG. 3. The components other than the second buffer space 14 and the fourth diffusion control part 15 provided between the gas inlet part and the first diffusion control part 13 are similar to those of the gas sensor 100 according to the first preferred embodiment so that the same reference numbers are applied and the description thereof is omitted.

Similarly to the first buffer space 12, the second buffer space 14 is an internal space provided in order to counteract concentration fluctuation of the measurement gas caused by pressure fluctuation of the measurement gas in the outside.

The fourth diffusion control part 15 introduces the measurement gas introduced into the second buffer space 14 through the gas inlets 10 and 11, into the first buffer space 12 with a predetermined diffusion resistance. The fourth diffusion control part 15 is provided as two horizontally-long slits, similarly to the first diffusion control part 13 and the second diffusion control part 30.

Appearance of the sensor element 101 according to the second preferred embodiment from a side of the forward end surface 101A is similar to that of shown in FIG. 2, that is, similar to that of the sensor element 101 according to the first preferred embodiment. As shown in FIG. 2, the first gas inlet 10 includes an opening 10a which is a horizontally-long slit (elongated and substantially rectangular) provided to make contact with a lower surface of the second solid electrolyte layer 6. The second gas inlet 11 includes an opening 11a which is a horizontally-long slit (elongated and substantially rectangular) provided to make contact with an upper surface of the first solid electrolyte layer 4.

In the gas sensor 100 according to the second preferred embodiment, the water droplets are prevented from entering into and attaching on the forward end surface 101A similarly to the gas sensor 100 according to the first preferred embodiment, in addition, the pressure fluctuation of the measurement gas rapidly introduced into the sensor element 101 due to air pulsation is effectively suppressed.

Similarly to the first preferred embodiment, the range of the sizes of the openings 10a and 11a where condensate water attached on the forward end surface 101A is preferably prevented from entering into the sensor element 101 and enough responsiveness of the sensor is ensured in the second preferred embodiment is shown below.

That is, with respect to the openings 10a and 11a, when letting the sum of the sizes x1 and x2 in the vertical direction be X, it is preferable to set the value of X obtained by adding x1 and x2 greater than or equal to 8 μm and less than or equal to 60 μm. It is further preferable to set the length X in a range of greater than or equal to 20 μm and less than or equal to 40 μm.

When letting the sum of areas of the openings 10a and 11a be S, it is preferable to set the value of S obtained by adding S1 and S2 greater than or equal to 0.02 mm$^2$ and less than or equal to 0.1 mm$^2$. It is further preferable to set the area S in a range of greater than or equal to 0.05 mm$^2$ and less than or equal to 0.08 mm$^2$.

Third Preferred Embodiment

In the gas sensor 100 according to the first and second preferred embodiments, the gas inlet part was constituted in a manner in which the first gas inlet 10 was formed to make contact with the lower surface of the second solid electrolyte layer 6, and the second gas inlet 11 was formed to make contact with the upper surface of the first solid electrolyte layer 4. In the third preferred embodiment, a mode in which the gas inlet part is constituted of only the second gas inlet 11 will be described.

Figure 4:
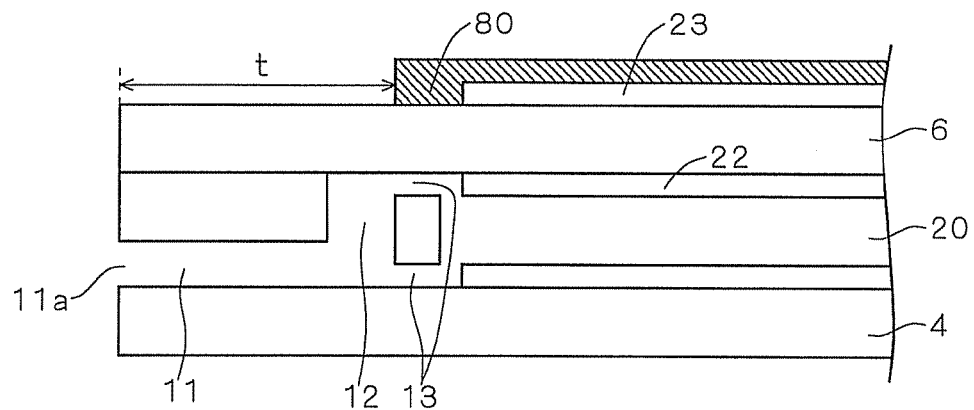
FIG. 4 is a partly enlarged view for schematically showing a configuration of a gas sensor according to a third preferred embodiment.
Figure 5:
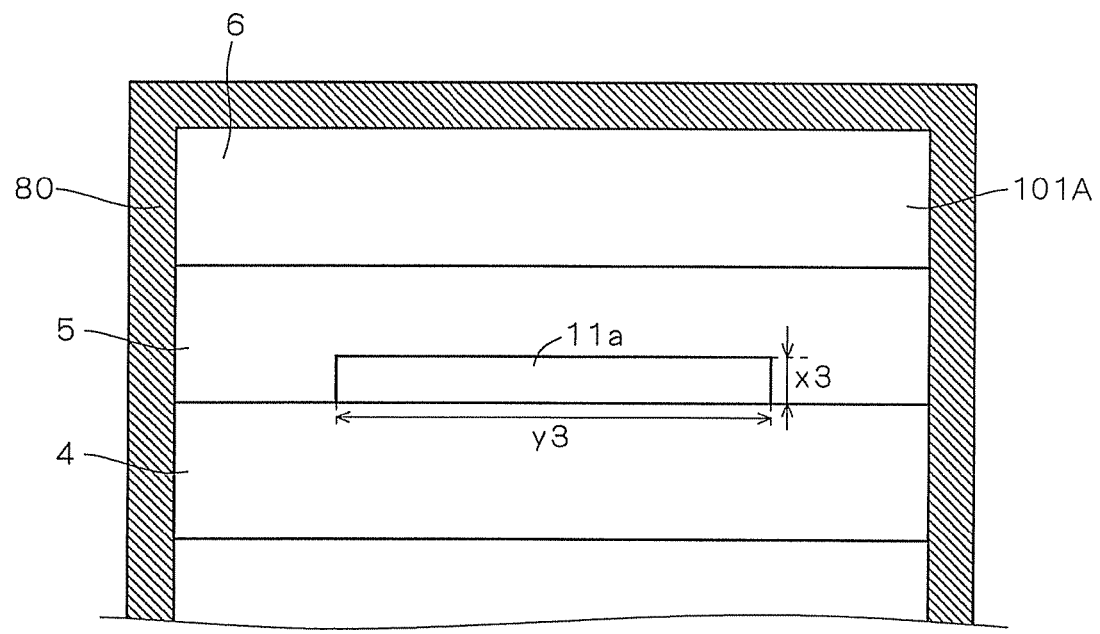
FIG. 5 is a view for showing a sensor element according to the third preferred embodiment seen from a side of the element end surface.

FIG. 4 is a partly enlarged view for schematically showing a configuration of the gas sensor 100 according to the third preferred embodiment. The gas sensor 100 shown in FIG. 4 is constituted with the gas inlet part including only the second gas inlet 11 in the gas sensor 100 according to the first preferred embodiment shown in FIG. 1, letting the size x1 in the vertical direction of the opening 10a be zero. Thus, FIG. 5 shows the appearance of the forward end surface 101A. In the present embodiment, as shown in FIG. 5, x3 indicates the size in the vertical direction of the opening 11a, and y3 indicates the size in the horizontal direction of the opening 11a. S3 represents an area of the opening 11a. In FIGS. 4 and 5, the gas sensor has the same configuration as the gas sensor according to the first preferred embodiment other than the first gas inlet 10 and the opening 10a so that the similar reference numbers are applied and the description thereof is omitted.

The range of the sizes of the opening 11a where condensate water attached on the forward end surface 101A is preferably prevented from entering into the sensor element 101 and enough responsiveness of the sensor is ensured in the third preferred embodiment is shown below.

That is, it is preferable to set the size x3 in the vertical direction of the opening 11a greater than or equal to 8 μm and less than or equal to 60 μm. It is further preferable to set the size x3 in a range of greater than or equal to 20 μm and less than or equal to 40 μm.

Also, it is preferable to set the area S3 greater than or equal to 0.02 mm$^2$ and less than or equal to 0.1 mm$^2$. It is further preferable to set the area S3 in a range of greater than or equal to 0.05 mm$^2$ and less than or equal to 0.08 mm$^2$.

Fourth Preferred Embodiment

In the fourth preferred embodiment, a mode in which the gas inlet part is constituted of only the first gas inlet 10 will be described.

FIG. 6 is a partly enlarged view for schematically showing a configuration of the gas sensor 100 according to the fourth preferred embodiment. The gas sensor 100 shown in FIG. 6 is constituted with the gas inlet part including only the first gas inlet 10 in the gas sensor 100 according to the second preferred embodiment shown in FIG. 3, letting the size x2 in the vertical direction of the opening 11a be zero. Thus, FIG. 7 shows the appearance of the forward end surface 101A. In the present embodiment, as shown in FIG. 7, x4 indicates the size in the vertical direction of the opening 10a, and y4 indicates the size in the horizontal direction of the opening 10a. S4 represents an area of the opening 10a. In FIGS. 6 and 7, the gas sensor has the same configuration as the gas sensor according to the second preferred embodiment other than the second gas inlet 11 and the opening 11a so that the similar reference numbers are applied and the description thereof is omitted.

The range of the size of the opening 10a where condensate water attached on the forward end surface 101A is preferably prevented from entering into the sensor element 101 and enough responsiveness of the sensor is ensured in the fourth preferred embodiment is shown below.

That is, it is preferable to set the size x4 in the vertical direction of the opening 10a greater than or equal to 8 μm and less than or equal to 60 μm. It is further preferable to set the size x4 in a range of greater than or equal to 20 μm and less than or equal to 40 μm.

Also, it is preferable to set the area S4 of the opening 10a greater than or equal to 0.02 mm$^2$ and less than or equal to 0.1 mm$^2$. It is further preferable to set the area S4 in a range of greater than or equal to 0.05 mm$^2$ and less than or equal to 0.08 mm$^2$.

<Variation>

The above describes the cases where there is one gas inlet and opening, or two gas inlets and openings in the sensor element, but the present invention is not limited to the above cases, but can be applied to the case where the sensor element has a configuration with three and above gas inlets and openings.

Example 1

In the present example, various gas sensors 100 each having different size in the vertical direction of the openings 10a and 11a (i.e. different area of the openings 10a and 11a) were prepared to carry out a test on responsiveness of the gas sensor and the effect of suppressing deterioration of the sensor output (i.e. deterioration of the measurement accuracy) when setting the sizes of the openings 10a and 11a in a preferable range.

Figure 8:
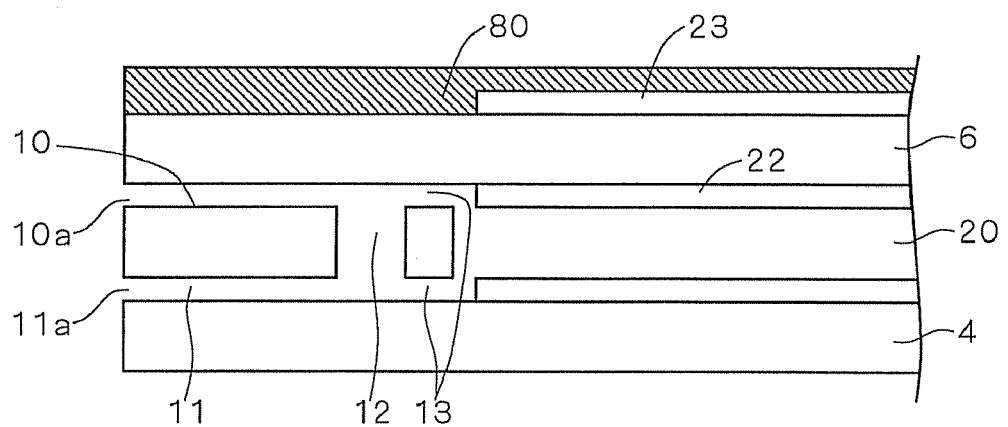
FIG. 8 is a partly enlarged view for schematically showing a configuration of a gas sensor according to an example 1.

In the example 1, the test was carried out using the gas sensor below. FIG. 8 is a partly enlarged view for schematically showing a configuration of the gas sensor according to the example 1. The gas sensor according to the example 1 is constituted to set a distance t of the gas sensor according to the first preferred embodiment as zero. A method of carrying out the test using the gas sensor according to the example 1 will be described hereinafter.

The sensor element was heated to approximately 100° C., setting the upper surface of the second solid electrolyte layer 6 of the gas sensor upside, and thereafter, magnesium nitrate solution (0.01 mol/kg) as a model of water droplets including contaminants was dropped on the element pump surface in order to create a situation where the water droplets including contaminants such as Mg were attached. A total of 10 ml magnesium nitrate solution was dropped for ten minutes.

Heating of the sensor element to approximately 100° C. is intended to recreate a heating situation in starting up an internal combustion such as automobile engine or the like, with the gas sensor according to the present embodiments being mounted on an emission system of the internal combustion in. When used in such a case, the gas sensor is kept at approximately 100° C. to prevent cracks from being generated. Then, after the gas sensor was dried, the evaluation was made on the responsiveness and the change of the sensor output.

The responsiveness of the gas sensor is evaluated by obtaining time (response time) from when the measurement gas is introduced from the gas inlet part until the measurement gas reaches the measuring electrode through the third diffusion control part 45, being subjected to a predetermined process in the gas distribution part, and thereafter it is detected by an ammeter 47 as a pump current Ip2. In the present example, the responsiveness was evaluated by dropping the above magnesium nitrate solution on the gas sensor according to the example 1, and a gas sensor according to a comparative example described below, and further calculating a ratio of the response time of the gas sensor according to the example 1 to that of the gas sensor according to the comparative example.

Figure 9:
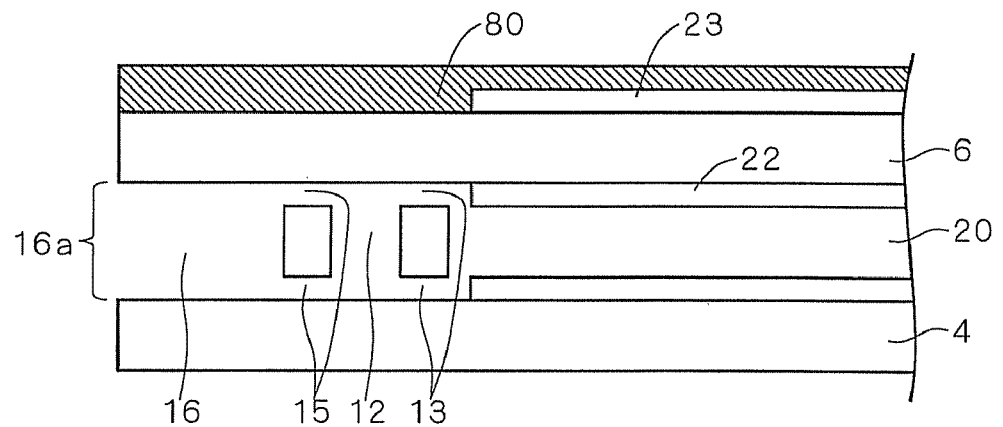
FIG. 9 is a partly enlarged view for schematically showing a configuration of a gas sensor according to a comparative example.
Figure 10:
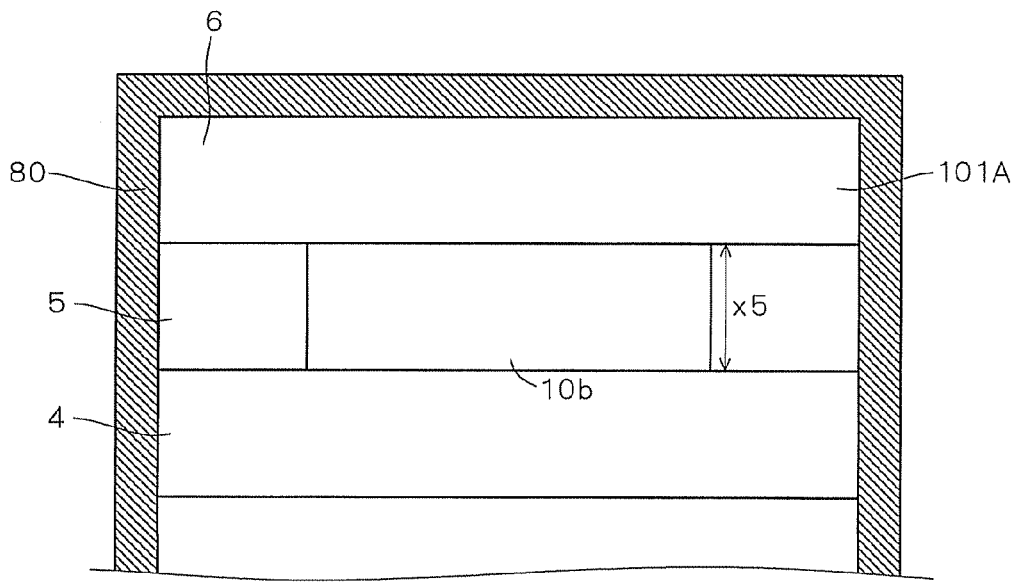
FIG. 10 is a view for showing a sensor element according to the comparative example seen from a side of the element end surface.

FIG. 9 is a partly enlarged view for schematically showing a configuration of the gas sensor according to the comparative example. The gas sensor according to the comparative example has the size in the vertical direction of the opening of the gas inlet part to be equal to a thickness of the spacer layer 5 in the constitution of the gas sensor 100 according to the second preferred embodiment. That is, the buffer space 14 according to the second preferred embodiment functions as a gas inlet 16 in the gas sensor according to the comparative example. The opening of the gas sensor according to the comparative example is shown as the opening 16a. The appearance of the forward end surface 101A in this case is shown in FIG. 10. A size x5 in the vertical direction of the opening of the gas sensor according to the comparative example is 0.2 mm, and area S5 of the opening is 0.5 mm$^2$.

The measurement of the response time is executed by measuring a time spent for detecting NO concentration change in the measurement gas as the pump current Ip2 by the ammeter 47, the NO concentration change being generated by pulse injection of air and NO while burning a liquefied natural gas and air, during measuring NOx concentration in a gas mixture including NOx with the gas sensor. As the response time is shorter, the responsiveness of the sensor is higher. In contrast, as the response time is longer, the response performance of the sensor is lower. In the present example, a temperature of a gas was set to be from 330° C. to 370° C., and a flow rate of a gas was set to be from 8 to 12 m/s.

Subsequently, with respect to the gas sensor according to the example 1 in which the above test for the response was carried out, the degree of change in the sensor output before and after magnesium nitrate solution was dropped was evaluated.

Specifically, with respect to the gas sensor according to the example 1, the extent of deterioration of the sensor output, i.e., the extent of deterioration of the measurement accuracy was evaluated by obtaining an amount of change of value of the pump current Ip2 when NO concentration in the measurement gas was varied, before and after magnesium nitrate solution (0.01 mol/kg) was dropped. The amount of change of the pump current Ip2 (sensor output) when NO concentration in the measurement gas was varied before magnesium nitrate solution was dropped in the gas sensor according to the example has been previously measured.

A gas mixture with nitrogen ($N_2$) including 3% of $H_2O$ (not including NO, i.e. gas mixture with NO concentration of 0 ppm) and a gas mixture including NO of 500 ppm in the above gas mixture were used as the measurement gas. A flow volume of a gas in measuring was set to be 5 L/min. and a temperature of a gas was set to be from 40° C. to 80° C.

When an output difference of the pump current Ip2 between in the cases where NO concentration is 0 ppm and where NO concentration is 500 ppm before magnesium nitrate solution is dropped is given as Di, and the output difference therebetween after magnesium nitrate solution is dropped is given as Df, a ratio D of output change is calculated by the following equation;

$$D=(Df-Di)/Di \qquad (1).$$

Figure 11:
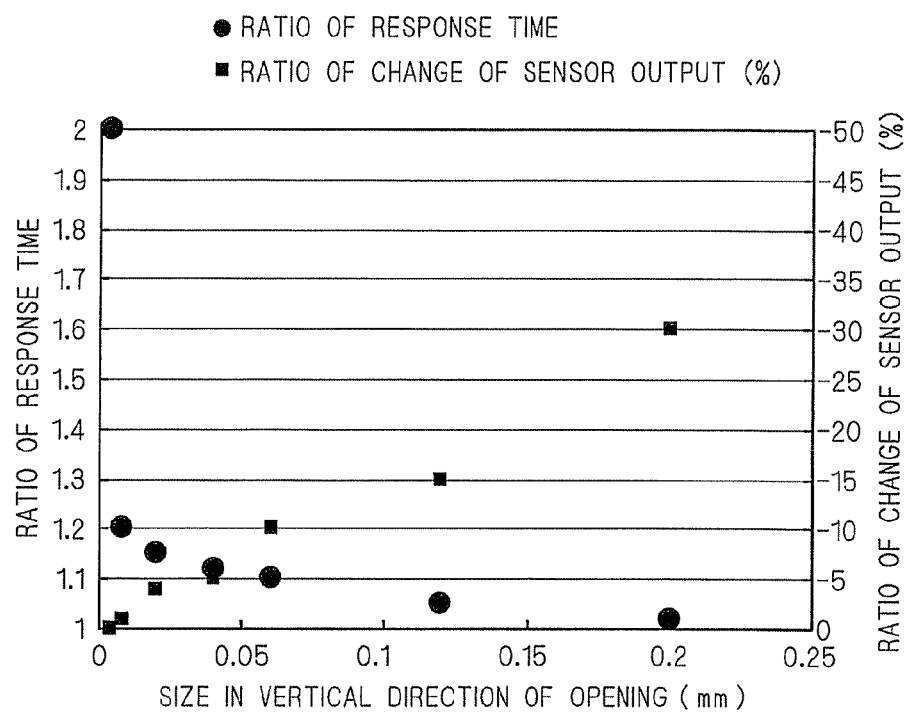
FIG. 11 is a view for showing the relation between a sum of a length of a vertical direction of an opening and a response of a sensor, and the relation between the sum of the length of a vertical direction of the opening and a change ratio of a sensor output.

FIG. 11 is a view for showing the relation between a sum of the size in the vertical direction of the opening and the responsiveness of the sensor, and the relation between a sum of the size in the vertical direction of the opening and a ratio of change of the sensor output. It has been confirmed that the ratio of the response time is within 1.2 and the change ratio of the sensor output is in a range within −10% when the sum of the size in the vertical direction of the opening is greater than or equal to 8 µm and less than or equal to 60 µm. When the ratio of the response time and the ratio of change of the sensor output is within such a range, condensate water attached on the forward end surface 101A can be prevented from entering into the sensor element 101 and the responsiveness of the sensor can be fully ensured.

Figure 12:
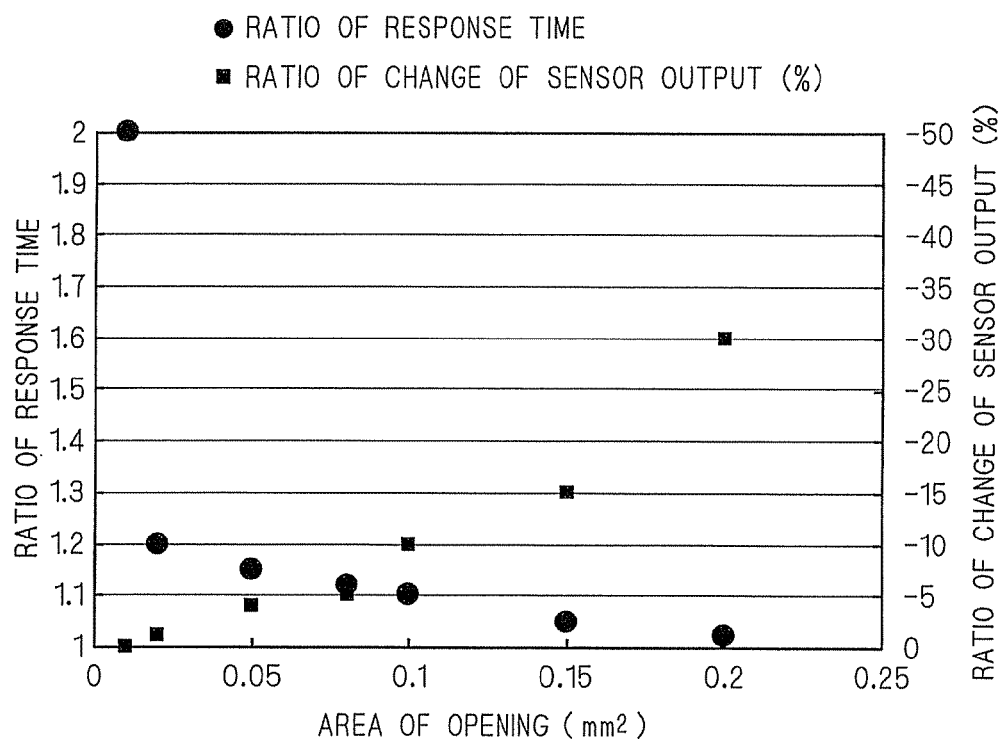
FIG. 12 is a view for showing the relation between a sum of an area of the opening and the response of the sensor, and the relation of the sum of the area of the opening and the change ratio of the sensor output.

FIG. 12 is a view for showing the relation between a sum of an area of the opening and the responsiveness of the sensor, and the relation between a sum of an area of the opening and a ratio of change of the sensor output.

Similarly to FIG. 11, in FIG. 12, it has been also confirmed that the ratio of the response time is within 1.2 and the ratio of change of the sensor output is in a range within −10% when the sum of the area of the opening is greater than or equal to 0.02 mm$^2$ and less than or equal to 0.1 mm$^2$. When the ratio of the response time and the ratio of change of the sensor output is within such a range, condensate water attached on the forward end surface 101A can be prevented from entering into the sensor element 101 and the responsiveness of the sensor can be fully ensured.

As can be seen, it has been confirmed that the gas inlet having a thickness and an area of the above preferable range makes the effect of preventing the water droplets from entering into the element, that is, suppressing deterioration of the sensor output and deterioration of the measurement accuracy which are caused by a clogging of the third diffusion control part 45 due to condensate water with contaminants entering into the element.

Example 2

In the present example, various gas sensors 100 each having a different distance t between the porous layer 80 and the forward end surface 101A are prepared to carry out a test on the effect of suppressing deterioration of a gas sensor output (i.e. deterioration of the measurement accuracy).

Figure 13:
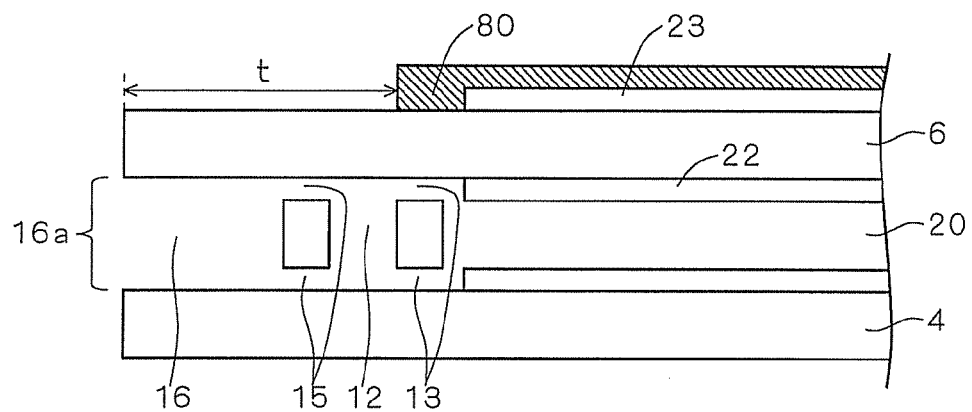
FIG. 13 is a partly enlarged view for schematically showing a configuration of a gas sensor according to an example 2.

In the example 2, the test was carried out using the gas sensor below. FIG. 13 is a partly enlarged view for schematically showing a configuration of the gas sensor according to the example 2. The test was carried out in the gas sensor shown in FIG. 13 with different distances t. The gas sensor according to the example 2 shown in FIG. 13 is differentiated from the gas sensor shown in FIG. 9 (gas sensor according to the comparative example in the example 1) in varying distance t.

The test was carried out with the similar method and condition to the evaluation of the change of the sensor output in the example 1. That is, with respect to the gas sensor according to the example 2, the extent of change of the sensor output, i.e., the extent of deterioration of the measurement accuracy was evaluated by obtaining an amount of change of each value of the pump current Ip2 when NO concentration in the measurement gas was varied before and after magnesium nitrate solution (0.01 mol/kg) is dropped. Also, the change ratio D of the sensor output was calculated by the equation (1), similarly to the example 1.

Figure 14:
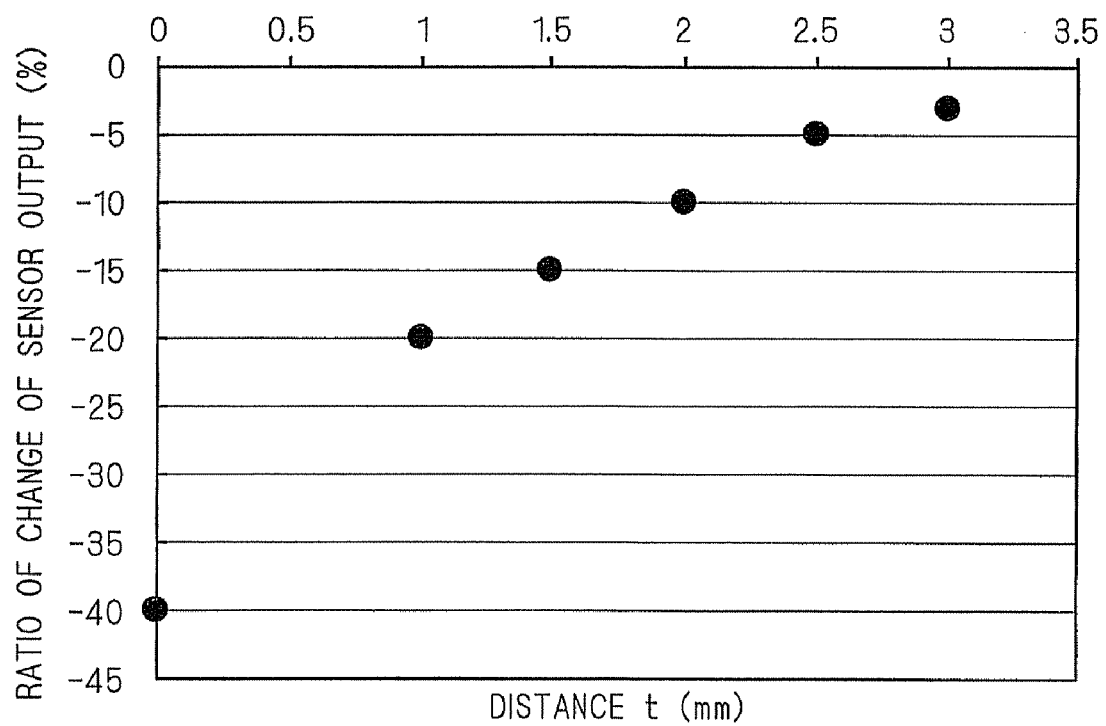
FIG. 14 is a view for showing the relation between a distance t and the change ratio of the sensor output.

FIG. 14 is a view for showing the ratio D of change of the sensor output to the distance t. The point where the distance t is zero shows the ratio of change of the sensor output in the gas sensor similar to the one shown in FIG. 9 (the gas sensor similar to the one according to the comparative example in the example 1).

As shown in FIG. 14, it has been confirmed that the ratio of change of the sensor output in the gas sensor according to the example 2 is smaller than that of the sensor element where the distance t is zero. It has been also confirmed that the ratio of change of the sensor output is from 0% to −10% when the distance t is greater than or equal to 2 mm. The water droplets can be prevented from attaching on the forward end surface 101A when the change ratio of the sensor output is within such a range.

From the above, it has been confirmed that it is more effective to suppress deterioration of the sensor output and deterioration of the measurement accuracy of the sensor caused by a clogging of the third diffusion control part 45 due to condensate water with contaminants entering into the element by dislocating the position of the porous layer 80 to the backward end of the sensor element in the distance t.

What is claimed is:

1. A gas sensor for detecting a predetermined gas component in a measurement gas, comprising:
   a sensor element;
   one or more openings provided at a forward end of said sensor element, for introducing the measurement gas from an outside of said sensor element, wherein said one or more openings are elongated and substantially rectangular, and a sum of sizes in a thickness direction of said one or more openings is greater than or equal to 8 µm and less than or equal to 60 µm; and
   a porous layer provided on a side surface of said sensor element so as to cover a region of said side surface to a back end of said sensor element, said porous layer consisting of a porous body having a higher porosity than a constituent material for said side surface of said sensor element,
   wherein said porous layer is positioned along the entirety of said side surface apart from said forward end of said sensor element by a distance greater than or equal to 2 mm,
   wherein said porous layer continuously extends towards and terminates at the back end of said sensor element, and
   wherein said side surface of said sensor element consists of a dense water-repellent material.

2. The gas sensor according to claim 1, wherein
   a sum of the sizes in the thickness direction of said one or more openings is greater than or equal to 20 µm and less than or equal to 40 µm.

3. The gas sensor according to claim 1, wherein
   a sum of an area of said one or more openings is greater than or equal to 0.02 mm$^2$ and less than or equal to 0.1 mm$^2$.

4. The gas sensor according to claim 3, wherein
   a sum of an area of said one or more openings is greater than or equal to 0.05 mm$^2$ and less than or equal to 0.08 mm$^2$.

5. The gas sensor according to claim 1, wherein
   a component of said porous body is at least one of alumina, magnesium alumina spinel and zirconia.

6. The gas sensor according to claim 1, wherein
   the gas sensor functions as a NOx sensor,
   said predetermined gas component is a nitrogen oxide gas, and
   a component of said sensor element is zirconia.

7. The gas sensor according to claim 1, wherein said porous layer is provided on at least two sides of said sensor element.

8. The gas sensor according to claim 7, wherein said porous layer is provided on all four sides of said sensor element.

9. A gas sensor for detecting a predetermined gas component in a measurement gas, comprising:
   a sensor element;
   one or more openings provided at a forward end of said sensor element, for introducing the measurement gas from an outside of said sensor element, wherein a sum of an area of said one or more openings is greater than or equal to 0.02 mm$^2$ and less than or equal to 0.1 mm$^2$; and
   a porous layer provided on a side surface of said sensor element so as to cover a region of said side surface to a back end of said sensor element, said porous layer consisting of a porous body having a higher porosity than a constituent material for said side surface of said sensor element,
   wherein said porous layer is positioned along the entirety of said side surface apart from said forward end of said sensor element by a distance greater than or equal to 2 mm,
   wherein said porous layer continuously extends towards and terminates at the back end of said sensor element, and
   wherein said side surface of said sensor element consists of a dense water-repellent material.

10. The gas sensor according to claim 9, wherein
    a sum of an area of said one or more openings is greater than or equal to 0.05 mm$^2$ and less than or equal to 0.08 mm$^2$.

11. The gas sensor according to claim 9, wherein
a component of said porous body is at least one of alumina, magnesium alumina spinel and zirconia.

12. The gas sensor according to claim 9, wherein
the gas sensor functions as a NOx sensor,
said predetermined gas component is a nitrogen oxide gas, and
a component of said sensor element is zirconia.

13. The gas sensor according to claim 9, wherein said porous layer is provided on at least two sides of said sensor element.

14. The gas sensor according to claim 13, wherein said porous layer is provided on all four sides of said sensor element.

* * * * *